US006368593B1

(12) United States Patent
Thompson

(10) Patent No.: US 6,368,593 B1
(45) Date of Patent: Apr. 9, 2002

(54) ENHANCED IMMUNOGENIC CELL POPULATIONS PREPARED USING H2 RECEPTOR ANTAGONISTS

(75) Inventor: James A. Thompson, Viejo, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/169,345

(22) Filed: Oct. 9, 1998

Related U.S. Application Data

(60) Provisional application No. 60/061,662, filed on Oct. 10, 1997.

(51) Int. Cl.[7] .......................... A01N 63/00; C12N 5/06; C12N 5/08; C12N 5/02
(52) U.S. Cl. .................. 424/93.71; 424/93.1; 424/93.3; 424/93.7; 435/325; 435/366; 435/372; 435/373; 435/347
(58) Field of Search .............................. 424/93.1, 93.3, 424/93.7, 93.71; 435/325, 366, 372, 373, 347

(56) References Cited

U.S. PATENT DOCUMENTS

| 4,716,111 A | 12/1987 | Osband et al. |
| 5,192,537 A | 3/1993 | Osband et al. |
| 5,569,585 A | 10/1996 | Goodwin et al. |
| 5,662,899 A | 9/1997 | Chokri et al. |

FOREIGN PATENT DOCUMENTS

| EP | 0 645 147 | 3/1995 |
| EP | 0 493 468 B1 | 4/1996 |
| WO | WO 95/20649 | 8/1995 |
| WO | WO 96/29394 | 9/1996 |
| WO | WO 98/16238 | 4/1998 |

OTHER PUBLICATIONS

Carpinito, et al., "Successful Adoptive Immunotherapy of Cancer Using In Vitro Immunized Autolougous Lymphocytes and Cimetidine," *Surgical Forum* vol. XXXVII, New Orleans (Oct. 1996).
Caprinito, et al., "Effective Treatment of Metastatic Carcinoma with In Vitro Immunized Autologous Lymphocytes and Cimetidine," *The Journal of Urology*, V. 133, No. 4, Part 2, p. 157A, Abstract 174 (Apr. 1985).
Osband, et al., "Improved Adoptive Cell Immunotherapy by Pre–Infusion Depletion of Suppressor Cells and In Vivo Suppressor Cell Blockade," *Proceedings of ASCO*, vol. 5, p. 232, Abstract 908 (Mar. 1986).
Palacios, et al., "Cimetidine Abrogates Suppressor T Cell Function In Vitro," *Immunology Letters*, vol. 3:33–37 (Dec. 1980).
Penhaligon, et al., "Antimetastatic Effect of Cimetidine on Mice Bearing a C3H Mouse Mammary Adenocarcinoma: Survival and Lymphocyte Function Studies," *Clin. Exlp. Matastasis*, vol. 2, No. 1:37–53 (1984).

Strausser, et al, "Lysis of Human Solid Tumors by Autologous Cells Sensitized In Vitro to Alloantigens," *The Journal of Immunology*, vol. 127, No. 1:266–271 (Jul. 1981).
*Animal Cell Culture: A Practical Approach*, R.I. Freshney, ed., IRL Press, Oxford, Table of Contents, pp. vii–xii (1987).
Carpinito et al., "Succesful Adoptive Immunotherapy of Cancer Using In Vitro Immunized Autologous Lymphocytes and Cimetidine," *Surg. Forum* 37:418–421(1986).
*Current Protocols in Immunology*, vol. I, J.E. Coligan et al., eds., John Wiley & Sons, Inc., Supplement 28, Table of Contents, pp. 1–9 (1998).
*Current Protocols in Nolecular Biology*, vol. I, F.M. Ausubel et al., eds., John Wiley & Sons, Inc., Table of Contents, Supplement 30, 39–40, pp. iii–xii (1995).
Damle et al., "Autologous Mixed Lumphocyte Reaction in Man. II. Histamine–Induced Suppression of the Autologous Mixed Lymphocyte Reaction by T–Cells Subsets Defined with Monoclonal Antibodies," *J. Clin Immunol.* 1:241–249 (1981).
Eisenthal, A. et al., "The Effect of Cimetidine on PBL from Healthy Donors and Melanoma Patients: Augmentation of T Cell Responses to TCGF* Mitogens and Alloantigens and of TCGF Production," *Cancer Immunol. Immunother*, 21:141–147 (1986).
Gifford et al., "Histamine Type–2 Receptor Antagonist Immune Modulation. I. Increased Cell–Mediated Cytotoxicity in normal and in Down–Regulated Systems," *Surgery* 10332):184–192 (1988).
Giulivi et al., "Effects of Cimetidine on In Vitro Transformation of Peripheral Monocytes to Macrophages in Healthy Volunteers and Cancer Patients," *Intl. J. Immunopharmacol.* 8:517–523 (1986).
Gold et al., "Adoptive Chemoimmunotherapy Using Ex Vivo Activated Memoory T–Cells and Cyclophosphamide: Tumor Lysis Syndrome of a Metastatic Soft Tissue Sarcoma," *Am. J. Hematol.* 44:42–47 (1993).
Gold et al., "Adoptive Chomoimmunotherapy for the Treatment of Relapsed and Refractory Solid Tumors Using Ex Vivo Activated Memory T Cells (Autolymphocyte Therapy) and Cyclophosphamide," *J. Immunother.* 13:213–221 (1993).
Gordon et al., "Cell Mediated Immune Response and Cimetidine," The Michigan Academician pp. 280–289 (1980).

(List continued on next page.)

Primary Examiner—Geetha P. Bansal
(74) Attorney, Agent, or Firm—Bozicevic Field & Francis LLP; Carol L. Francis

(57) ABSTRACT

This invention provides a method to enhance alloactivation in a mixed lymphocyte culture. Alloactivated cells are effective in treating tumors when implanted into a tumor site or coinjected with tumor cells as a vaccine. By enhancing alloactivation, more cell combinations achieve a threshold of activation adequate for use in therapy, and the level of cytokine secretion in proliferative phase cultures is generally increased.

8 Claims, 5 Drawing Sheets-

OTHER PUBLICATIONS

Graham et al., "The USe of Ex Vivo–Activate dMEmory T Cells (Autolymphocyte Therapy) in the Treatment of Metastatic Renal Cell Carcinoma: Final Results From a Radomized, Controlled Multisite Study," *Sem. Urol. 1127*–34 (1993).

Lavin et al., "Autolymphocyte Therapy for Metastatic Renal Cell Carcinoma: Initial Clinical Results From 335 Patients Treated in a Multisite Clinical Practice," *Transplant. Proc. 24*:3059–3064 (1992).

Marshall et al., "Effects of Coumarin (1,2–Benzaopyrone) on Lymphocyte, Natural Killer Cell, and Monocyte Functions In Vitro," *J. Biol. Resp. Modifiers 8*:70–85 (1989).

McCarty, M.F., "Addendum: Cimetidine as an Adjuvant for Allogeneic Lymphocyte Immunotherapy of Cancer" *Medical Hypotheses 17*:155–156 (1985).

*Methods in Enzymology,* vol. LVIII, Cell Culture, W.B. Jakoby et al., eds., Academic Press, New York, Table of Contents, pp. v–viii (1979).

Miller, J.M. & Calos, M.P. eds., "Gene Transfer Vectors for Mammalian Cells" Table of Contents, pp. vii–ix (1987).

*Molecular Cloning: A Laboratory Manual,* Second Edition, J. Sambrook et al., eds., Cold Spring Harbor Laboratory Press, Table of Contents, pp. xi–xxxviii (1989).

*Oligonucleotide Synthesis: A Practical Approach,* M.J. Gait, ed., IRL Press, Oxford, Table of Contents, pp. vii–xii (1984).

Osband et al., "Effect of Autolymphocyte Therapy on Survival and Quality of Life in Patients with Metastatic Renal–Cell Carcinoma," *Lancet 335*:994–998 (1990).

Osband et al., "Succesful Tumour Immunotherapy with Cimetidine in Mice," *Lacet i*:636–638 (1981).

Plaut et al., "Properties of a Subpopulation of T Cells Bearing Histamine Receptors," *J. Clin. Invest. 55*:856–874 (1975).

*Remington's Pharmaceutical Sciences,* 18 Edition, A.R. Gennaro, ed., Mack Publishing Co., Easton, PA, Table of Contents, pp. xv–xvi (1990).

Richtsmeier et al., "Selective, Histamine–Mediated Immunosuppression in Laryngeal Cancer," *Ann. Otol, Phinol. Laryngol. 96*:569–572 (1987).

*The Polymerase Chain Reaction,* K.B. Mullis et al., eds., Birkhäuser, Boston, MA, Table of Contents, pp. xv–xvii (1994).

*Weir's Handbook of Experimental Immunology,* Fifth Edition, vol. I, Immunochemistry and Molecular Immunology, D.M. Weir et al., eds., Blackwell Science, Cambridge, MA, Table of Contents, pp. v–vii (1996).

ENHANCED IMMUNOGENIC CELL POPULATIONS PREPARED USING H2 RECEPTOR ANTAGONISTS

REFERENCE TO RELATED APPLICATIONS

This application claims the priority benefit of U.S. provisional patent application Ser. No. 60/061,662, filed Oct. 10, 1997, pending. The priority application is hereby incorporated herein by reference in its entirety.

FIELD OF THE INVENTION

The present invention relates generally to the fields of cellular immunology and cancer therapy. More specifically, it relates to the preparation of immunogenic alloactivated cell compositions and the use of H2 receptor antagonists to affect lymphocyte interaction.

BACKGROUND

Significant progress has been made at the frontier of human cancer therapy by the development of new immunogenic compositions. A promising development has been the use of alloactivated lymphocytes in recruiting the host's participation in the elimination of tumor cells.

One example is the method of treating tumors described in International application WO 95/20649. Alloactivated lymphocytes are prepared by collecting peripheral blood mononuclear cells from a healthy, unrelated donor, and stimulated in a mixed lymphocyte reaction with leukocytes of a cancer patient. At about the time of peak cytokine secretion, the cultured cells are harvested, prepared for human administration, and implanted into the bed of the tumor. The implanted cells apparently stimulate a host versus graft rejection, which then refocuses on bystander tumor cells to palliate the disease condition.

Another example is cancer immunotherapy using tumor cells combined with mixed lymphocytes, described in detail in International application WO 9816238. In this technology, third-party donor cells that have been alloactivated in culture are mixed with inactivated cancer cells from the patient, and administered intramuscularly as a vaccine. The host immune system is actively recruited by the alloactivated cells, and generates a specific systemic response against tumor antigen components present in the composition.

Both these technologies involve preactivation of the implanted lymphocytes. Not all combinations of human responder and human stimulator cells result in an equally strong alloreaction. Accordingly, there is a need to develop techniques to enhance the strength of alloreaction in the preparative cultures of immunogenic cells.

Type 2 receptors for the vasoactive amine histidine (H2 receptors) are present on several different cell types. In areas of medical research unrelated to the inventions described above, H2 receptor antagonists such as cimetidine have been used to affect immune function.

Properties of subpopulations of T cells bearing histamine receptors was described in the mid 1970's (e.g., Plaut et al., J. Clin. Invest. 55:856, 1975; reviewed in Gordon et al., Michigan Academician 12:281, 1980). Experiments with H1 and H2 agonists and antagonists indicated that histamine-induced activation of suppressor T cells and the production of soluble suppressor factors were mediated through H2 receptors (Damle et al., J. Clin Immunol. 1:241, 1981). Eisenthal et al. (Cancer Immunol. Immunother. 21:141, 1986) showed that cimetidine augmented proliferation induced by allogeneic cells. Giulivi et al. (Int. J. Immunopharmacol. 8:517, 1986) showed that the addition of cimetidine to cultures of peripheral blood mononuclear cells enhanced monocyte transformation, possibly by blocking H2 receptors of T suppressor cells. Gifford et al. (Surgery 103:184, 1988 showed that cell-mediated cytotoxicity (CMC) is also increased by cimetidine in normal and down-regulated mouse splenocytes, and reverses CMC suppression by suppressor cells in a dose-dependent manner.

Cimetidine has been administered in various combination therapies to reverse suppression of anti-tumor immunity. See, for example, Osband et al. (Lancet 335:994, 1990), Marshall et al. (J. Biol. Resp. Modifiers 8:70, 1989), Richtsmeier et al. (Ann. Otol. Rhinol. Laryngol. 96:569, 1987, Osband et al. (Lancet i:636, 1981), Graham et al. (Sem. Urol. 11:27, 1993), Gold et al. (Am. J. Hematol. 44:42, 1993), Gold et al. (J. Immunother. 13:213, 1993), Carpinito et al. (Surg. Forum 37:418, 1986.), and Lavin et al. (Transplant. Proc. 24:3059, 1992).

U.S. Pat. No. 5,192,537 outlines a method of treating renal cell carcinoma using activated mononuclear cells, renal tumor antigen and cimetidine. Immunoreactive cells are sensitized for an antigenic marker associated with a malignant tumor in vitro. The activation involves collecting mononuclear cells from the patient, depleting suppressor T cells, suspending the mononuclear cells with autologous serum, and culturing the cells under conditions that immunize the cells against the tumor of the patient. The cells are then infused into the patient to treat the tumor. Optionally, in order to improve the efficacy of the cells, suppressor cells in the patient are inactivated by treating the patient with cimetidine.

U.S. Pat. No. 4,716,111 describes a process for producing human antibodies. Mononuclear cells are depleted of suppressor T cells bearing H2 receptors by binding to albumin-linked cimetidine. The remaining lymphocytes are then exposed to antigen, autologous serum, and a nonspecific lymphocyte activator. Examples proposed for activators are pokeweed mitogen, phytohemagglutinin, or supernatant from mixed lymphocyte cultures thought to contain allogenic effect factor.

U.S. Pat. No. 5,662,899 describes macrophages with enhanced cytotoxic activity by culturing in a medium containing a $D_3$ vitamin and GM-CSF. Optionally, the medium used in the culturing of the macrophages also contains indomethacin or cimetidine.

International Patent Application WO 95/20649 relates to the ex vivo activation of immunoreactive cells. The proposed process involves contacting a first sample of mononuclear cells from a patient with OKT3 (anti-CD3 antibody) to produce an OKT3-derived culture supernatant, which is then used to activate a second cell sample. The suppressor cells in the mononuclear cell population may be functionally inactivated using cimetidine to inactivate suppressor cells and indomethacin to inactivate suppressor activity of monocytes.

European Patent Application EP 645147 outlines a method involving identifying and removing active lymph nodes in a patient having a tumor, and culturing the lymph node cells to obtain tumor-specific lymphocytes. Lymph node cells were expanded by incubating under various culture conditions. Biological response modifiers in the medium included IL-1, IL-2, IL-4, IFN-γ, OKT3 anti-CD3 antibody, indomethacin, and cimetidine (Example III). Calculated expansion indices indicated that cimetidine at 100 μg/mL did not significantly alter expansion or phenotype at any time in the culture.

SUMMARY OF THE INVENTION

It has been discovered that adding H2 receptor antagonists to the medium of a preparative mixed lymphocyte culture increases the strength of the alloactivation within the first three days of the culture period. Extent of alloactivation at early culture times can be characterized by several functional criteria, including tetrazolium reduction, CD69 expression, intracellular esterase, and cytokine secretion. Enhanced cytokine secretion in turn is predicted to render the alloactivated cultures more effective for cancer treatment.

Accordingly, embodiments of the invention include a method for increasing the level of cytokine secretion, esterase activity, or CD69 expression by alloactivated lymphocytes, particularly during the first few days of alloactivation, comprising adding to the medium of an ex vivo culture of responder lymphocytes and allogeneic stimulator cells an H2 receptor antagonist.

Also embodied is a method of preparing a cultured cell population containing alloactivated human donor lymphocytes for treating a tumor or eliciting an anti-tumor immunological response in a human patient, comprising the steps of coculturing human lymphocytes allogeneic to the human patient with human leukocytes so as to alloactivate the lymphocytes, and harvesting the cocultured cells from culture at a time when the harvested cells, upon implantation in the bed of a solid tumor in the patient, are effective in the treatment of the tumor; wherein an H2 receptor antagonist is included in the culture medium. Compositions prepared according to this method are beneficially administered at or around the site of a solid tumor in a patient, with or without prior resection or partial resection of the solid tumor.

Also embodied is a method for preparing a cultured cell population containing alloactivated human donor lymphocytes for treating a tumor or eliciting an anti-tumor immune response in a human patient, comprising the steps of coculturing human lymphocytes allogeneic to the human patient with human leukocytes so as to alloactivate the lymphocytes, and combining the cocultured cells with tumor cells from the human patient or their progeny, progeny thereof, wherein an H2 receptor antagonist is included in the culture medium. Compositions prepared according to this method are beneficially administered in the form of an injectable cellular vaccine.

A non-limiting list of cancers suitable for treatment using compositions prepared according to these methods include melanoma, pancreatic cancer, liver cancer, colon cancer, prostate cancer, and breast cancer.

DETAILED DESCRIPTION

It is an objective of this invention to improve the strength of the alloreaction in mixed lymphocyte cultures, particularly during the early proliferative phase of culture, near the time when cytokine secretion peaks.

Figure 3:
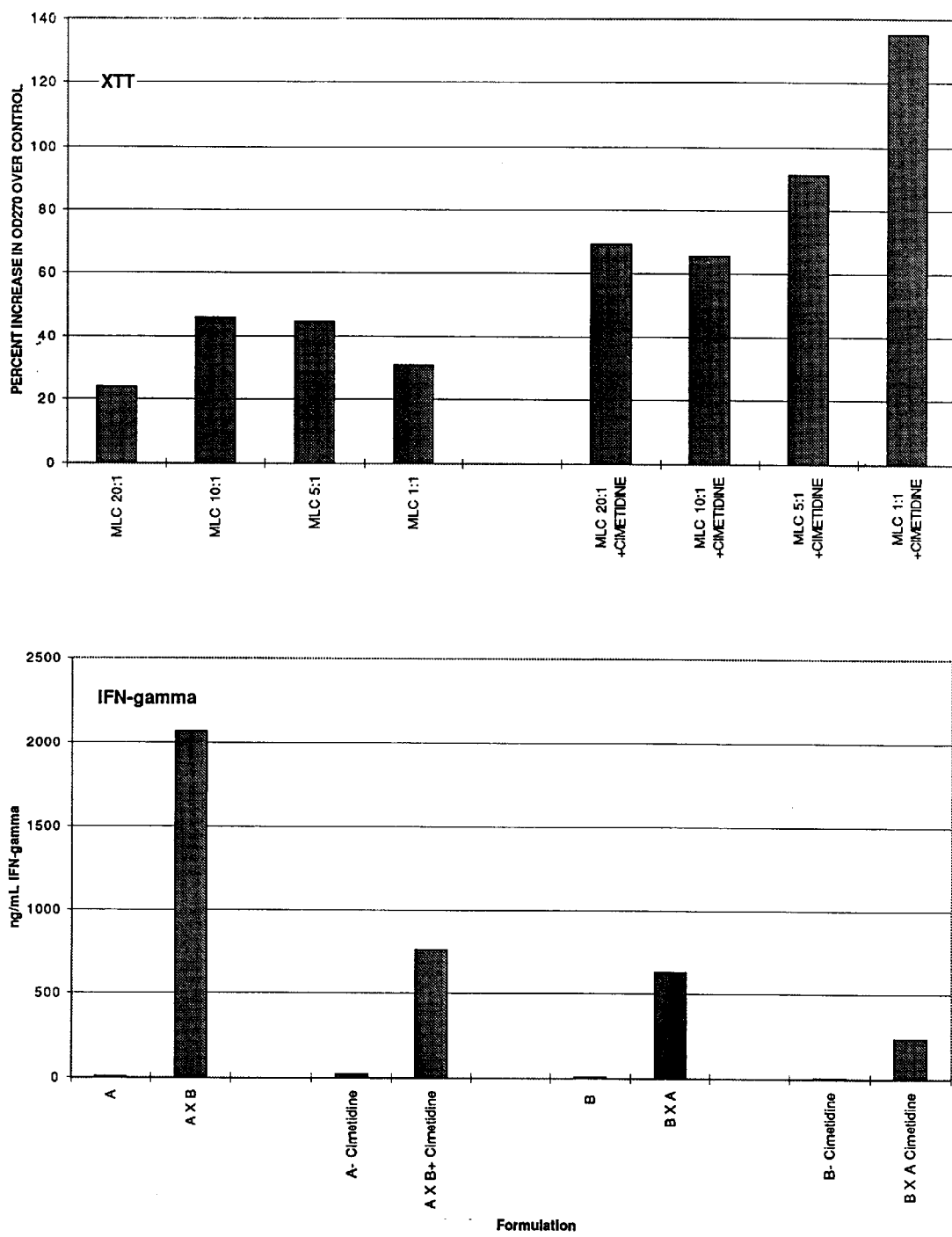
FIG. 3 is a bar graph showing the effect of cimetidine on activation of human lymphocytes in culture. Upper panel shows the effect as measured in an XTT Formazan Reduction Assay. Lower panel shows the level of IFN-γ detected by immunoassay.

An illustration is provided in FIG. 3. Human peripheral blood mononuclear cells were cultured at a 10:1 ratio of responder: stimulator cells at $0.5 \times 10^6$ cells/mL. The graph shows the functional read-out after 3 days in culture, using a Formazan reduction assay. Responder or stimulator cells cultured alone show little effect by addition of histamine (a suppression mediator) or the histamine antagonist cimetidine at the outset of the culture. However, cimetidine enhanced the signal observed in the assay by about 3-fold.

Accordingly, H2 antagonists can be included in the medium of mixed lymphocyte culture whenever early manifestations of alloactivation are desired. H2 antagonists are particularly useful in the enhancement of preparative mixed lymphocyte cultures conducted during the preparation of allostimulated cells for immunotherapy. Enhancement is achieved in terms of the number of cell combinations that can be measurably alloactivated, increasing the range of cell:cell combinations that can be used to prepare therapeutic compositions. Enhancement is also achieved by the strength of the alloreactivity, which possibly correlates with effectiveness.

A further description of preferred methods of this invention are provided in the sections that follow.

Definitions

"Mixed lymphocyte reaction", "mixed lymphocyte culture", "MLR", and "MLC" are used interchangeably in this disclosure to refer to a mixture comprising a minimum of two different cell populations that are allotypically different. At least one of the allotypically different cells is a lymphocyte. The cells are cultured together for a time and under suitable conditions to result in the stimulation of the lymphocytes. A frequent objective of an MLC is to provide allogeneic stimulation such as may initiate proliferation of the lymphocytes; but unless indicated, proliferation during the culture is not required. In the proper context, these terms may alternatively refer to a mixture of cells derived from such a culture. When cells from an MLC are administered as a bolus to a human, especially in a tumor bed, it is referred to as a "cytoimplant".

The terms "vaccine", "immunogen", or "immunogenic composition" are used herein to refer to a compound or composition, as appropriate, that is capable of either: a) generating an immune response against an antigen (such as a tumor antigen) in a naive individual; or b) reconstituting, boosting, or maintaining an immune response in an individual. The immunological response may comprise antibodies, immunoreactive cells (such as helper/inducer or cytotoxic cells), or any combination thereof, and is preferably directed towards an antigen that is present on a tumor towards which the treatment is directed.

A "cell line" or "cell culture" denotes higher eukaryotic cells grown or maintained in vitro. It is understood that the descendants of a cell may not be completely identical (either morphologically, genotypically, or phenotypically) to the parent cell.

"Inactivation" of a cell is used herein to indicate that the cell has been rendered incapable of cell division to form progeny. The cell may nonetheless be capable of response to stimulus, or biosynthesis or secretion of cell products such as cytokines. Methods of inactivation are known in the art. Preferred methods of inactivation are treatment with toxins such as mitomycin C, or irradiation. Cells that have been fixed or permeabilized and are incapable of division are also examples of inactivated cells.

The term "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

An "effective amount" of a therapeutic composition is sufficient to effect a beneficial or desired clinical result, particularly the generation of an immune response, or noticeable improvement in clinical condition. An immunogenic amount is an amount sufficient in the subject group being treated (either diseased or not) sufficient to elicit an immunological response, which may comprise either a humoral response, a cellular response, or both. In terms of clinical response for subjects bearing a neoplastic disease, an effective amount is amount sufficient to palliate, ameliorate, stabilize, reverse or slow progression of the disease, or otherwise reduce pathological consequences of the disease. An effective amount may be given in single or divided doses. Preferred quantities and cell ratios for use in an effective amount are given elsewhere in this disclosure.

General Techniques

The practice of the present invention will employ, unless otherwise indicated, conventional techniques of molecular biology, microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds. 1994); "Current Protocols in Immunology" (J. E. Coligan et al., eds., 1991). See also Gately et al., Lee et al., and Zarling et al. (infra) for examples of techniques in mixed lymphocyte cultures. General procedures for the preparation and administration of pharmaceutical compositions are outlined in *Remington's Pharmaceutical Sciences* 18*th Edition* (1990), E. W. Martin ed., Mack Publishing Co., PA.

All patents, patent applications, articles and publications mentioned herein, both supra and infra, are hereby incorporated herein by reference.

Preparation of Alloactivated Cell Populations

H2 receptor antagonists can be used to enhance certain functional properties of cells being allostimulated in a mixed lymphocyte reaction. The process involves alloactivating one or more responder cell populations containing lymphocytes with one or more stimulator cell populations expressing alloantigens by including the H2 receptor antagonist in the culture medium.

Source of Leukocytes:

The cells that are used to prepare the composition can be taken from healthy donors or human patients, such as those bearing tumors treatable with an alloactivated cell culture.

Responder and stimulator cell populations are allogeneic to each other. Cells are generally described as allogeneic if they are from the same species but bear a phenotypic difference sufficient to stimulate an alloreaction. Any qualitative difference in the identity of MHC allotypes between cells of the same species means they are allogeneic cells. In humans, differences at any of the HLA-A, B, C, D, DP, DQ, and DR loci constitute allotypic differences that may stimulate alloactivation in a manner that can be enhanced in the presence of H2 receptor antagonists. Identity of HLA-A, B, C, DP, DQ, and DR phenotypes is typically determined using allotype-specific antibodies in a cytotoxicity or immunofluorescence technique.

Preferred allotypic differences for the purposes of the present invention relate to HLA class II antigens. Comparing the class II antigens of the DP, DQ, and DR loci between the putative allogeneic cells and cells of the subject to be treated, preferably at least 1, and increasingly more preferably 2, 3, 4, 5, or even 6 loci are different between allogeneic cells. Class II antigens may also be determined at the D locus by mixed lymphocyte reaction using typed cells. Donors of allogeneic cells are generally unrelated to the subject being treated, to maximize the number of MHC mismatches. In a normal outbred population, unrelated individuals will almost invariably differ at a number of different loci.

The "responder" cells are capable of specifically reacting to an allogeneic stimulus. The cell population generally contains lymphocyte cells or cells of the lymphocyte lineage, particularly T cells. Lymphocytes expressing CD4 antigen (CD4+ cells), and cells expressing CD8 antigen (CD8+ cells) are both included in the definition of T lymphocytes, and either or both may be included in the composition. Generally, the responder cells are leukocytes obtained from peripheral blood, typically enriched for mononuclear cells (PBMC), and optionally further enriched for cells of the lymphocyte lineage.

The "stimulator" cells are allogeneic to the responder cells and capable of eliciting an alloreaction in the responders. Suitable cell types for use as stimulator cells are those that bear a high density of allogeneic histocompatibility antigens, particularly class II antigens. Any type of cell (not limited to blood cells) bearing sufficient alloantigens can be used. A particularly suitable source is peripheral blood leukocytes or white cells. It is desirable to enrich for, or at least not to deplete cells expressing class II histocompatibility antigens from the population, such as B cells and monocytes. Extensive subfractionation of the cells is not usually required, and a simple peripheral blood mononuclear cell population (PBMC) is adequate for most purposes.

The combined cell population is not necessarily restricted to one source for the responder cells and one source for the stimulator cells. Two, three, four, or a higher plurality donors may optionally be used to facilitate collection of the allogeneic cells, to increase stimulation of the allogeneic cells, to minimize the elicitation of an anti-allotype response when administered to a subject, or to otherwise enhance the therapeutic efficacy of the preparation.

Collection and Preparation of Donor Cells:

Donors are typically prescreened to identify those with sufficient leukocyte count, and exclude those with neoplastic conditions or transmissible infections. Collection may be performed by whole blood donation followed by separation of blood cell populations, or by leukapheresis. Leukapheresis is especially appropriate for collecting the responder cell population, because the number of cells required is substantial.

For the preparation of therapeutic amounts of alloactivated lymphocytes, sufficient blood is processed to obtain about 100–500 mL leukapheresis suspension, preferably at least about 200 mL. For example, leukapheresis may be performed using a Cobe 2997 (COBE SPECTRA®, Lakewood Colo.); Fenwall CS 300 (Fenwall, Deerfield Ill.); or Haemonetrics (Braintree Mass.) blood cell separator. Flow rates of ~40–50 mL/min for 2–4 h yield ~200–250 mL leukapheresis suspension having <1 mL red cells, with variations between individual donors and the equipment used.

The collected leukocytes are generally washed to remove platelets, and resuspended in a suitable medium, such as AIM V supplemented with 2% inactivated fetal calf serum. Separation of PBMC and other enrichment procedures include centrifugation over a suitable medium such as FICOLL™, passage over a nylon-wool column, affinity separation methods such as panning, or sorting in a fluorescent cell sorter using an antibody against a relevant cell-surface marker. Where possible, it is generally preferable to decrease the number of manipulation steps. For example, better leukapheresis separation may obviate the need for subsequent separation on FICOLL™.

Mixed Lymphocyte Cultures:

Responder and stimulator cells are combined in a suitable culture medium, typically supplemented with fetal calf serum or a serum substitute, and optionally including other growth factors. The ratio of responder:stimulator cells depends on the nature of the intended application. For the preparation of alloactivated lymphocytes for tumor therapy, typical ratios are about 20:1 to 5:1. Where there are a plurality of stimulator or responder cells in a one-way MLC, the same approximate ratio of responders:stimulators is maintained. Thus, when using multiple stimulators, the ratio may be approximately 9:(1:1) or 8:(1:1:1).

This invention encompasses the use of two-way or multi-way mixed lymphocyte cultures, wherein a plurality of cell populations act as both responders and stimulators. In certain embodiments of the invention, one-way MLCs are performed by inactivating the stimulator cells, for example, by treating ~$10^7$ cells/mL with 50 µg/mL mitomycin C or sublethal irradiation, followed by washing. One-way activation of multiple responders can be achieved by conducting a separate culture for each responder population, and then combining the alloactivated cells just before use.

Once combined in the desired ratio, the cells cultured at an appropriate density in a suitable atmosphere (such as 95% $O_2$, 5% $CO_2$ at about 37° C.). The culture period depends on the ultimate use of the composition. For preparation of terminally differentiated cytotoxic T lymphocytes or helper/inducer cells, culture periods are typically 5 days or longer, and may optionally be supplemented by further additions of stimulator cells or soluble factors. For alloactivated cells used for eliciting an anti-tumor response in a subject, the culture is harvested around the time of peak cytokine secretion; i.e., between about 24 h and 72 h, depending on culture ratios and other conditions.

The recitation within this disclosure of preferred cell sources, cell ratios, culture conditions, timing, and other features, is intended as an aid to the practitioner and is not meant to limit the scope of the invention, unless explicitly required.

Measuring Functional Criteria of the Alloactivated Cell Population:

The strength of alloactivation in mixed lymphocyte cultures can be determined using one or more functional assays.

Since cytokine secretion is believed to play an important role in certain therapeutic compositions, cytokines can be tested in a standard immunoassay. Particular cytokines of interest are IL-2, IL-4, IL-6, TNF-α, LT, IFN-γ, G-CSF, M-CSF (both membrane and secreted form), and GM-CSF. For example, particular degrees of stimulation is indicated by levels of biological activity of TNF-α or LT at 50–150 U/mL, or 500–3500 pg/mL.

Proxies for functional activity of the alloactivated cells include: I: MTT Formazan Reduction Assay; II: XTT Formazan Reduction Assay; III: Flow Cytometry for CD3/CD69 or CD3/FDA; IV: FDA Plate Assay; V: Acid Production Assay. These assays are detailed in Example 3. More traditionally, alloactivation can be determined by cell proliferation, measured by culturing a test sample for 5 days and conducting a standard [$^3$H]-thymidine uptake assay, or by counting blast cells. The predictive value of functional assays can be determined by comparing results of the assays on cultured cells with the effect of the cells in a suitable animal model. Preferred cultures for use in cancer immunotherapy show a level of activation $\geq 10\%$ above unstimulated donor control value within one of the first 3 days of culture, as measured by the Tetrazolium Reduction Assay (XTT), or by Flow Cytometry (CD69) or intracellular esterase, or both.

Enhancing Alloactivation with H2 Receptor Antagonists

Experience in animal model experiments shows that not all third-party donors provide the same degree of alloactivation when third party donor are used for both the stimulator and responder cells.

The prototype H2 receptor antagonist used in the experiments in the Example section is cimetidine (TAGAMET®). Other H2 receptor antagonists include rantidine, famotidine, and nizatidine. H2 receptor agonists include 4-methyl histamine (4MH) and dimaprit (DIM). These compounds are readily available from commercial pharmaceutical suppliers.

Adding an H2 receptor antagonist to the culture medium of the mixed lymphocyte reaction has an enhancing effect on alloactivation during the first three days of culture. This is illustrated in Example 5. Without intending to be bound by theory, it is hypothesized that the H2 receptor antagonist inhibits the activity of suppressor T cells in the culture. Thus, it is especially effective in restoring alloactivation to cell combinations that are clearly incompatible, but show little reactivity in a standard MLC.

A preferred H2 receptor antagonist is cimetidine, added to the culture medium at between about 1 µg/mL and 500 µg/mL, preferably about 5 µg/mL to 100 µg/mL, and typically about 20 µg/mL. The antagonist can be added to the culture at any time, but generally has a maximal effect if included in the medium at the outset of the culture. Adjustment of the amount and timing for various culture conditions and cell combinations can be determined empirically using the functional assays outlined in the preceding section.

Use of Enhanced Alloactivated Cells

Cell populations prepared in mixed lymphocyte reactions enhanced according to this invention can be used whenever a high or more rapid alloactivation is desirable.

In one example, an H2 antagonist can be included in the medium of a cell typing reaction, which is then read by an early functional assay such as those described in this disclosure. In another example, an H2 antagonist can be included in the medium of a preparative culture of cytokines, to enhance the level of factors secreted early in the response. In a third example, an H2 antagonist can be included in the medium of a culture to enhance the early expression of certain cell-surface markers, which can then be used to separate the cells into different subpopulations.

H2 antagonists are particularly useful in preparative mixed lymphocyte cultures conducted during the preparation of allostimulated cells for immunotherapy. One application of alloactivated cells is the treatment of tumors or eliciting of an anti-tumor immune response by implanting them into the bed of a tumor. This approach to immunotherapy is described in more detail in International Application WO 95/20649, which is hereby incorporated herein by reference in its entirety. Another application of alloactivated cells is to combine them with tumor cells from a patient, and adminster them to the patient as an injectable cellular vaccine composition. This approach to immunotherapy is described in more detail in International Application WO 9816238, which is hereby incorporated herein by reference in its entirety.

One purpose of these types of immunotherapy is to elicit an immune response which may play a role in eradication of the tumor or palliation of the disease. The immune response may include either humoral or cellular components, or both. Humoral immunity can be determined by a standard immunoassay for antibody levels in a serum sample from the treated individual.

A general cellular immune response can be measured as the T cell proliferative activity in cells (particularly PBL) sampled from the subject after administration. Inactivated tumor cells, preferably derived from the subject, are used as stimulators A non-specific mitogen such as PHA serves as a positive control; incubation with an unrelated stimulator cell serves as a negative control. After incubation of the PBMCs with the stimulators for an appropriate period (typically 5 days), [$^3$H]thymidine incorporation is measured. T cell cytotoxicity (CTL) can also be measured using $^{51}$Cr-labeled tumor cells as targets.

Another purpose of immunotherapy is for treatment of a neoplastic disease, particularly cancer. Evidence of a host response can be shown inter alia by infiltration of host leukocytes (such as lymphocytes, histiocytes, and other leukocytes) into the tumor site by standard histomorphology analysis.

Appropriate doses and modes of administration are outlined in more detail in the aforementioned patent publications, and illustrated below in Example 5. The dose given is an amount "effective" in bringing about a desired therapeutic response, be it the stimulation of an immune response, or the treatment of cancer as defined elsewhere in this disclosure. The various components of a cell implant or cellular vaccine are present in an "effective combination", which means that there are sufficient amounts of each of the components for the vaccine to be effective.

Timing of administration of compositions of this invention is within the judgment of the managing physician, and depends on the clinical condition of the patient, the objectives of treatment, and concurrent therapies also being administered. Suitable means of immunological monitoring include a one-way MLR using patient's PBL as responders and primary tumor cells as stimulators. An immunological reaction may also be manifest by a delayed inflammatory response at the injection site. Suitable means of monitoring of the tumor are selected depending on the tumor type and characteristics, and may include CT scan, magnetic resonance imaging (MRI), radioscintigraphy with a suitable imaging agent, monitoring of circulating tumor marker antigens, and the subject's clinical response. Additional doses may be given, such as on a monthly or weekly basis, until the desired effect is achieved. Thereafter, and particularly when the immunological or clinical benefit appears to subside, additional booster or maintenance doses may be given as required.

During the course of therapy, the subject is evaluated on a regular basis for general side effects such as a febrile response. Side effects are managed with appropriate supportive clinical care.

The examples presented below are provided as a further guide to a practitioner of ordinary skill in the art, and are not meant to be limiting in any way.

EXAMPLES

Example 1: Measurement of the Degree of Alloactivation

In order to ensure the production of high quality effective MLC cells, a method of measuring the potency of the alloactivated cells can be employed. Only cell cultures with activity over and above unstimulated control cells should be used clinically. It is beneficial to compare the activity to the unstimulated control, since baseline activity of mononuclear cells from different individuals varies widely.

Several methods are available for measuring lymphocyte activation. Compared with unstimulated mononuclear cells, alloactivated cells reduce more Formazan dye and have more esterase activity. Turnover of XTT (a Formazan dye) can be easily demonstrated in a 96-well plate by calorimetric spectrophotometry at 470 nm (reference 650 nm). Activated cells typically show higher absorbance than controls. Lymphocyte activation can also be demonstrated by flow cytometric determination of esterase activity using the esterase substrate, fluorescein diacetate (FDA). T cells with high esterase are not determined using FDA and a Phycoerythrin-labeled CD3 antibody. Esterase activity can be accurately measured in a plate assay by using higher concentrations of FDA and determination of esterase activity by spectrophotometry at 494 nm (reference 650 nm) in a 96-well plate format. Background esterase activity inherent to serum-containing media is inhibited by addition of a competitive esterase inhibitor (~10 mM), arginine methyl ester. For the most part, these measures show good correlation with each other and with blastogenesis.

I: MTT Formazan Reduction Assay

This assay is used to enumerate live cells by ability for culture sample to reduce MTT to blue-green Formazan dye, and is also helpful for the distinguishing activated from inactive cells. It can be used for practically any cell in practically any media. The useful cell range is between $10^5$ and $5 \times 10^6$ per mL.

Reagents:

96 well plates, flat bottom (not ELISA plates)

5 mg/mL MTT (Sigma) in PBS (frozen)

20% SDS in 45% DMF, 0.2 N HCl (pre-warmed to 37° C.)

Procedure:

Place 100 µL of culture media with cells in 96 well plate in duplicate or triplicate. Use 100 µL of media alone for controls. Leave first column blank.

Add 10 µL of MTT to each well. Tap plate to mix. Cover plate and incubate 37° C. for 4 hours.

Add 50 µL of SDS solution, avoiding bubbles. Tap to mix. If bubbles are present, blow on surface. Count plate at 570 nm (reference 650 nm).

II: XTT Formazan Reduction Assay

This assay is used to enumerate live cells by ability for culture to sample to reduce XTT to red-orange Formazan dye, and is also helpful for the distinguishing activated from inactive cells. It can be used for practically any cell in practically any media. The useful cell range is between $10^5$ and $5 \times 10^6$ per mL.

Reagents:
  96 well plates, flat bottom (not ELISA plates)
  1 mg/mL MTT (2,3-bis (2-methoxy-4-nitro-5-sulfophenyl-2H-tetrasolium-5-carboxanilinide salt, Sigma) in PBS (fresh)
  1.53 mg/mL PMS (phenylmethanesulfonyl fluoride, Sigma) in PBS (frozen, protected from light)

Procedure:
  Place 100 µL of culture media with cells in 96 well plate in duplicate or triplicate. Use 100 µL of media alone for controls. Leave first column blank.
  Pre-mix PMS with XTT immediately before use (5 µL per mL XTT). Add 50 µL of XTT to each well. Tap plate to mix.
  Cover plate and incubate 37° C. for 4 hours. Count plate at 470 nm (reference 650 nm).

III: Flow Cytometry for CD3/CD69 or CD3/FDA

This is a measurement of T lymphocyte activation after mixed lymphocyte alloactivation. Activities such as CD69 expression or esterase activity correlate with cytokine secretion and can be used as surrogate measures of lymphocyte activity. Unstimulated lymphocytes do not express surface CD69 and have only low levels of nonspecific esterases. Once activated by allo-antigens or non-specific mitogens, the expression of CD69 appears within 48 hours (peak at 24). Esterase activity increases shortly after stimulation, and continues for several days. Not all allostimulated lymphocyte reactions proceed with the same kinetics, and it is preferable to measure activation on day 1, 2 and 3 of the culture.

Sample:
  Test samples of donor and patient cells are mixed in small cultures at $0.5 \times 10^6$ cells/mL in 2% FCS-RPMI. These cultures are maintained at 37° C. in 5% $CO_2$ incubator until testing.

Reagents:
  Monoclonal antibodies:
  CD3-PE (Coulter)
  CD69-FITC (Becton-Dickinson). Keep refrigerated when not in use and protect from light.
  Fluorescein Diacetate (Sigma): Stock solution is prepared at 10 mg/mL DMSO, protected from light, and stored in frozen lot tested aliquots. Make working solution weekly by diluting stock 1:100 in DMSO, keep working solution refrigerated and protected from light.
  D-PBS, 0.5% paraformaldehyde-0.05% TRITON™ X-100 in PBS Procedure:
  Internal control unstimulated and activated mononuclear cells samples are produced on an as-needed basis. Large lot-tested batches will be frozen in 250 µl aliquots in 10% DMSO freezing media.
  Mononuclear cells from a normal donors can be used to produce activated control specimens. These cells are placed in 2% FCS-RPMI at $0.5 \times 10^6$ cells/mL up to 100 mL. Cells are cultured for 2 days at 37° C. in the presence or absence of 2 µg/mL PHA lectin, or admixed at a ratio of 10:1 with a second donor population. The cells are collected by centrifugation at 350 X g for 5 minutes. The media is removed and replaced by 1/10th the volume of DMSO Freezing media, and frozen. When needed, control unstimulated and stimulated cells can be thawed quickly and resuspended at the original volume by adding 9 volumes of PBS.

Control cells are analyzed according to the protocol below along with samples from the test culture. The duplicate use of control specimens is an addition quality assurance measure. The percentage of CD69 or esterase positive lymphocytes should be within a 5% variance.

Dilute 5 µL of CD3-PE antibody (per sample) in 0.5 mL PBS (per sample). Add either 10 µL CD69 (per sample) or 1 µL of working solution of FDA (per sample).

To 12×75 mm labeled polystyrene tubes, deliver 0.5 mL of diluted antibody. Add 100 µL of well mixed sample to each tube, including reference controls, unstimulated donor cells and the allo-activated cells. Gently vortex and incubate 30 minutes at room temperature. Add 0.5 mL of 0.5% paraformaldehyde-0.05% TRITON™ X-100 PBS and mix.

Counting is performed on an appropriately equipped flow cytometer, such as the EPICS XL Coulter Flow Cytometer. Histogram 1 (forward scatter vs. CD3) of either protocol should have a generous gate around the CD3+ mononuclear cells. Region A should approximate % T-Lymphocytes and should be passed to Histogram 2. In Histogram 2, the use of side scatter versus CD3 permits discrimination of lymphocytes (low side scatter level) from unlysed RBSs, RBC ghosts, platelet aggregates, residual granulocytes and/or other debris. A gate is drawn around the lymphocytes (see Histogram 2 for example). This second gate is passed to Histogram 3, where the CD3+ CD69+ cells or CD3+ FDA+ cells are displayed. Run the control values first to set gates (unstimulated controls). Place the quad stat cursor of Histogram 3 so that the CD69 or FDA high values (Quad 2) are 2%. Leave this gate set when analyzing stimulated samples.

Count at least 5,000 gated cells for each sample to obtain a 97% confidence interval.

IV: FDA Plate Assay

This assay is used to enumerate live cells by ability for culture sample to turnover the esterase substrate, fluorescein diacetate, and is also helpful for the distinguishing activated from inactivated cells. This assay can be used for practically any media. The useful cell range is between $10^5$ and $5 \times 10^6$ per mL.

Reagents:
  96 well plates, flat bottom (not ELISA plates)
  10 mg/mL FDA (Sigma) in DMSO (stock, protect from light)
  10 mg/mL Arginine methyl ester (Sigma) in DMSO Procedure:
  Place 100 µL of culture media with cells in 96 well plate in duplicate or triplicate. Use 100 µL of media alone for controls.
  Make a fresh working solution of FDA by adding 10 µL per mL of PBS of stock FDA plus 50 µL AME stock per mL. Add 20 µL of FDA working solution to each well. Tap plate to mix.
  Cover plate and incubate 37° C. for 1 hour. Count plate at 494 nm (reference 650 nm).

V: Acid Production Assay

This assay is used to quantitate relative organic acid production in cultures. This correlates with the state of activation of cells. This assay requires the use of medium containing no more than 2% serum. Practical cell range is $1-5 \times 10^6$ cells/mL incubated from 24–48 hours.

Reagents:
  96 well plates, flat bottom (not ELISA plates)
  Acid Analysis Reagent. This is made in bulk and stored at 4° C. Add 0.1 mg/mL Bromophenol Blue in distilled water. Add sufficient concentrated HCl until the appropriate titration point is met. Titration is performed until yellow-green color is obtained after adding 75 μL of reagent to 100 μL RPMI 2% FCS in a well of a 96 well plate.

Procedure:

Place 100 μL of culture media with cells in 96 well plate in duplicate or triplicate. Use 100 μL of media alone for controls.

Add 75 μL of Reagent to each well. Tap plate to mix. Count plate at 470 nm (reference 650 nm).

VI: Blastogenesis Quantitation

This assay is used to quantitate the absolute number of lymphoblasts produced in cultures after 7 days. This assay can be used for peripheral blood mononuclear cells in practically any media. The useful cell range is between $1 \times 10^5$ and $5 \times 10^6$ per mL.

Reagents:

Wright's Stain or Diff-Quick Stain

Procedure:

Place 1–2 drops of a 7 day culture in a Cytospin chamber and perform Cytospin. Stain dried glass slide with either Wright's Stain or Diff-Quick Stain. Count number of lymphoblasts and other cells under oil immersion 100× lens of microscope. Count over 300 total cells.

Example 2: Alloactivation Using Cultured Human Cells

Criteria for Functionality of Alloactivated Cells

The degree of alloactivation (a potential reflection of potency in therapy) can be measured according to the functional assays detailed in Example 3. This example illustrates the degree of activation revealed by the assays.

Human peripheral blood monocytes were isolated from samples taken from a number of unrelated human volunteers, and set up in one-way mixed lymphocyte cultures at a 10:1 responder:stimulator ratio as described elsewhere in this disclosure. The assays were run after 2–3 days in culture.

Compared with unstimulated mononuclear cells, alloactivated cells have more esterase activity and reduce more XTT (a Formnaan dye). Esterase activity can also be measured by flow cytometry using the esterase substrate, fluorescein diacetate (FDA). T cells with high esterase activity can be identified by Phycoerythrin-labeled CD3 antibody in conjunction with FDA. These measures correlate well with blastogenesis (determined after culturing for one week), or the level of IL-2 or IFN-γ in the supernatant.

Impact of Using Multiple Allogeneic Stimulator Cells

Allo-activated human lymphocyte cultures were produced using cells from either one, two, three or four unrelated donors. $3 \times 10^6$ cells/mL were cultured in 2% FCS-RPMI at 37° C. for 2 days. Two-donor populations were produced by admixing responder cells with stimulator cells at a 10:1 ratio. Populations containing three or four donor cells were produced by mixing responder cells with two or three different stimulator cells at ratios of 9:1:1 or 8:1:1:1.

Figure 1:
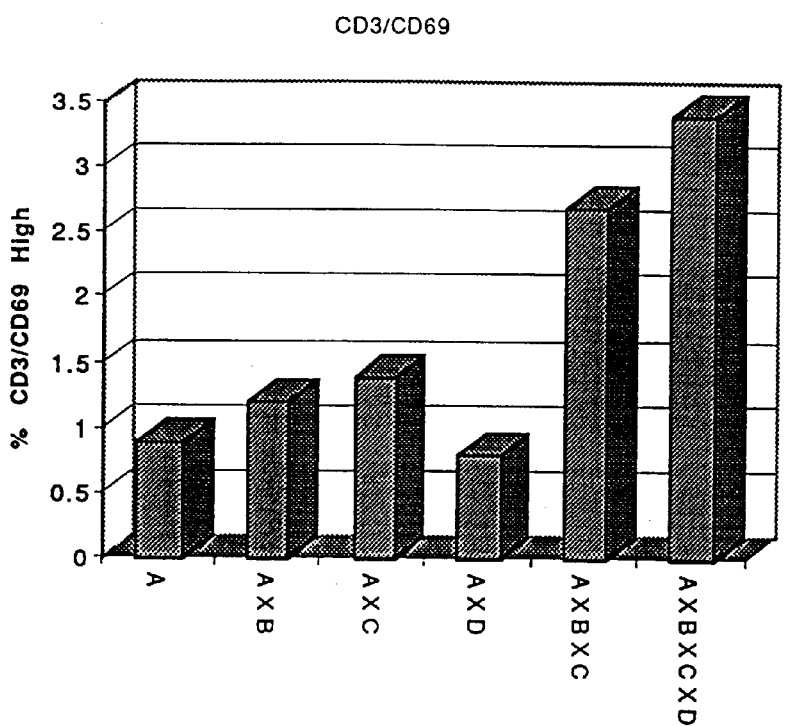
FIG. 1 is a bar graph showing the level of alloactivation of human lymphocytes (measured by anti-CD69 or fluorescein diacetate staining) achieved using different combinations of responder and stimulator cells.
Figure 1:
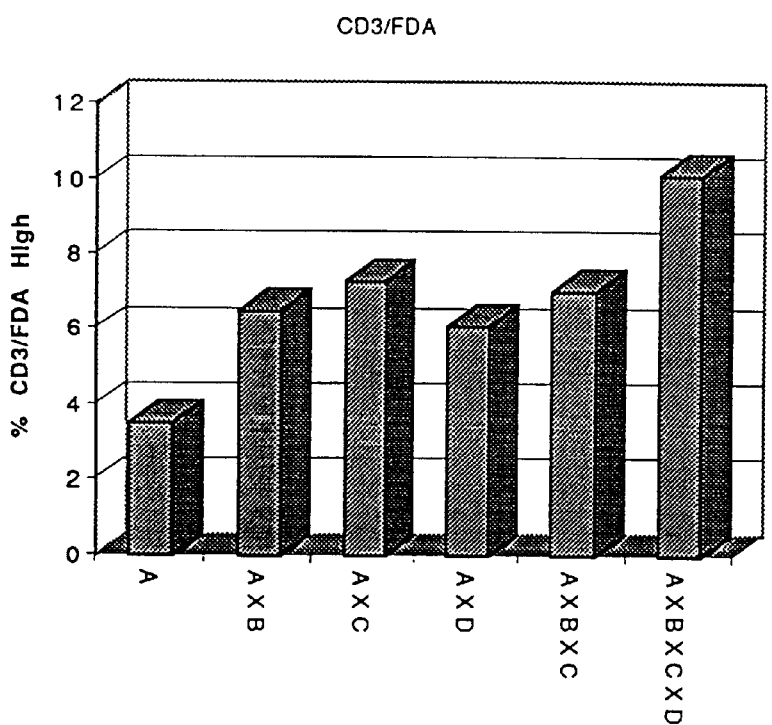

FIG. 1 shows the characteristics of the cells measured using flow cytometry. All values represent percentage of brightly fluorescent cells after counting 4000 cells on a Coulter EPICS XL Cytometer.

The results show that cultures prepared with stimulators from a plurality of donors in certain conditions reach higher levels of activation.

Example 3: Effect of Cimetidine on Alloactivation of Human Lymphocytes

Histamine is known to induce the activity of T suppressor cells. Since T suppressor cells can play a role in controlling the activity of the MLR, the effect of histamine and of a potent histamine type 2 (H2) receptor blocking drug, Cimetidine, was tested in alloreacting cell cultures. Cell populations composed of alloactivated human peripheral blood mononuclear cells were produced using cells from unrelated donors. All cultures contain a 10:1 ratio of responder:stimulator mononuclear cells at $0.5 \times 10^6$ cells/mL. In some cultures, 20 μ/mL histamine or 20 μg/mL Cimetidine were added on day 0.

Figure 2:
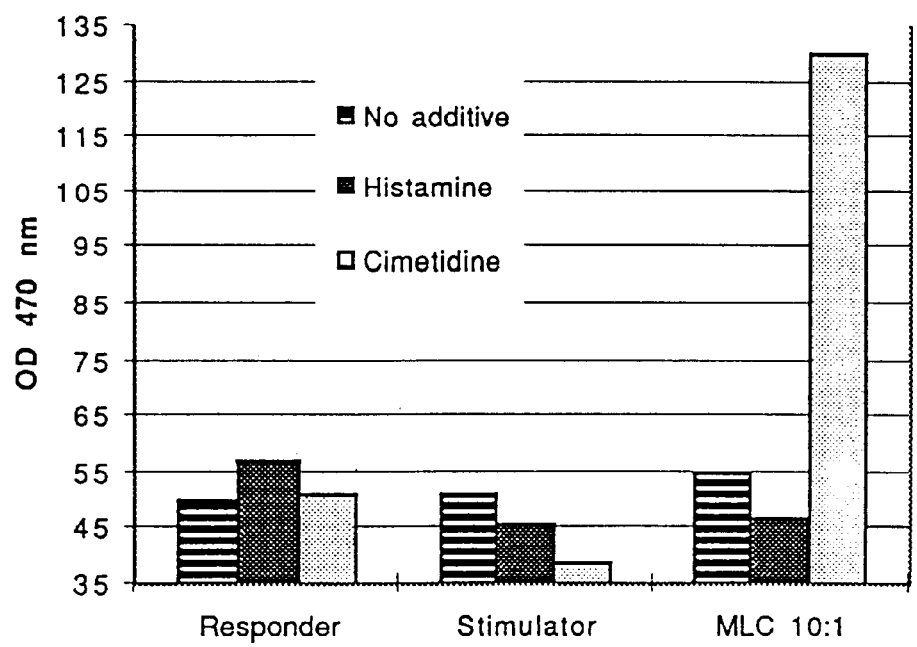
FIG. 2 is a bar graph showing the effect of including 20 µg/mL of histidine (dark shading) or cimetidine (light shading) into cultures of human cells; either the responder alone, the stimulator alone, or mixed cultures at a responder:stimulator ratio of 10:1.

FIG. 2 shows the results measured using a Formazan reduction (XTT) assay. Histamine induced suppression and decreased strength of the allo-activation. Cimetidine enhanced activity, possibly by blocking the development of suppression.

Impact of Cimetidine on Activation Measured by Formazan Reduction

An XTT Formazan Reduction assay was performed on mixed lymphocyte cultures prepared using human peripheral blood mononuclear cells from two unrelated donors after 2 days in culture at 37° C. in RPMI 2% FCS. Cell cultures were formulated at the indicated ratios of Responder (Donor #1) to Stimulator (Donor #2) in the presence or absence of 20 μg/mL Cimetidine.

FIG. 3 (upper panel) shows the percentage of increased absorbance at 470 nm relative to cultures of responder cells alone. This particular combination of cells induced only a modest reaction that did not increase much with cell ratio. However, Cimetidine had a profound effect on XTT activity, especially on cultures of the higher ratios.

Impact of Cimetidine on IFN-γ Production

An IFN-γ specific ELISA was performed to quantitate the secretion of IFN-γ into supernatants of cultured human peripheral blood mononuclear cells. Cells were cultured at 10:1 ratio of Responder (Donor #A) to Stimulator (Donor #B) cells, or vise-versa, in the presence or absence of 20 μg/mL Cimetidine. Results were measured after culturing for 3 days a5 37° C. in RPMI containing 2% FCS.

FIG. 3 (lower panel) shows that more IFN-γ was made by Donor A in response to B, than by Donor B in response to Donor A. Cimetidine lowered the amount of IFN-γ secreted after 3 days in both MLRs.

Impact of Cimetidine on IL-2 Production

An Interleukin-2 specific ELISA was performed to quantitate the production of IL-2 in supernatants of cultured human peripheral blood mononuclear cells after 3 days at 37° C. in RPMI-2% FCS. Cells were cultured at the 10:1 ratio of Responder (Donor #A) to Stimulator (Donor #B), or vise-versa, in the presence or absence of 20 μg/mL Cimetidine.

Figure 4:
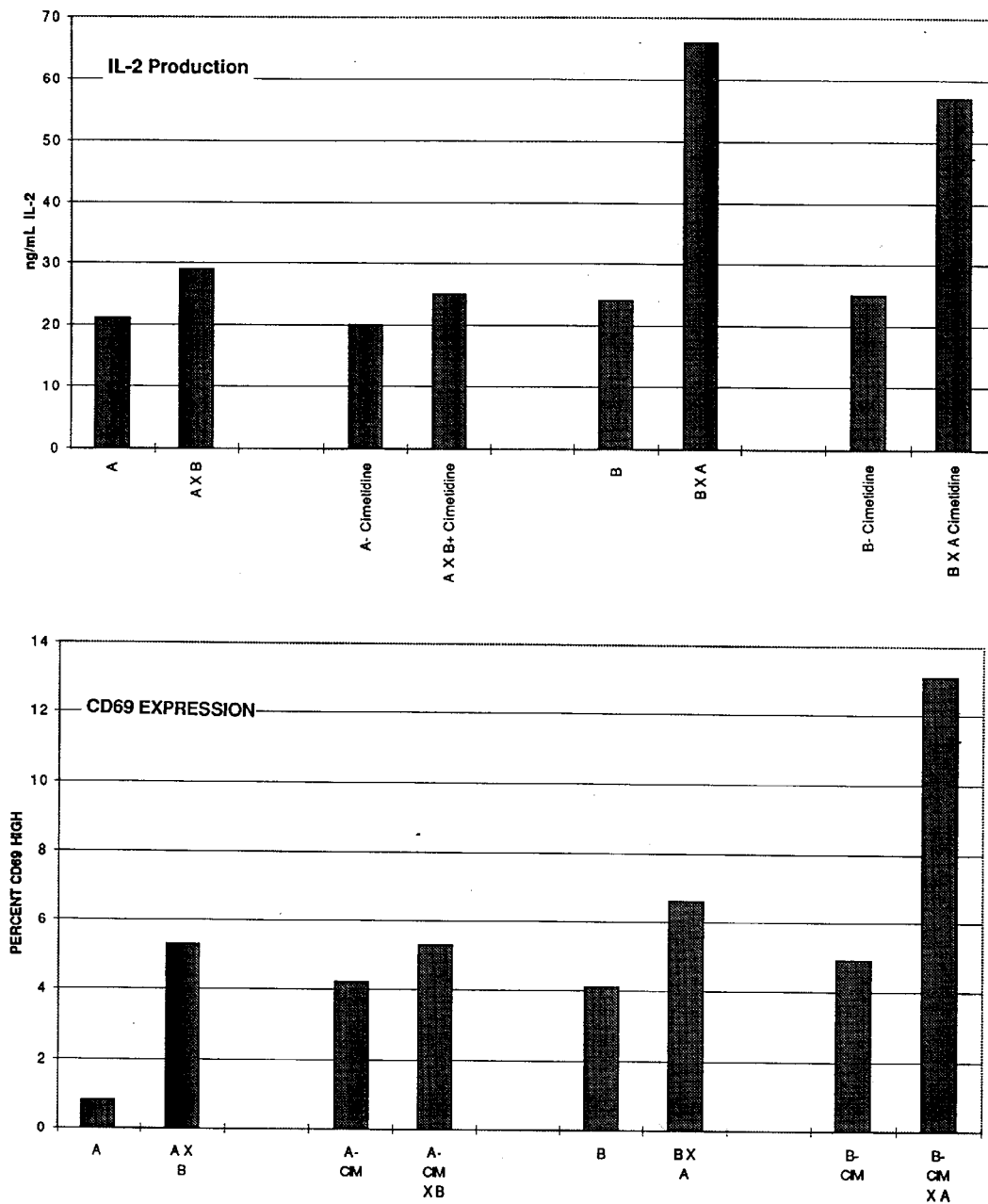
FIG. 4 is a bar graph showing the effect of cimetidine on activation of human lymphocytes in culture. Upper panel shows the level of IL-2 detected by immunoassay. Lower panel shows the level of CD69 expression, determined by flow cytometry.

FIG. 4 (upper panel) shows that more IL-2 is made by Donor B in response to A, than by Donor A in response to Donor B. These are the same supernatants used to quantitate IFN-γ. Cimetidine raised the amount of IL-2 secreted after 3 days in both MLRs.

Impact of Cimetidine on CD69 Expression

Flow Cytometry was used to quantitate the level of CD69 expression in the cell cultures used to quantitate IFN-γ or IL-2.

Results are shown in FIG. 4 (lower panel). While the overall response seems similar between responder A and responder B, the background control unstimulated response by B is higher. This suggests that B responds less to A than the converse. Cimetidine enhanced CD69 expression by some but not all of the cultured cells.

Example 4: Animal Modeling of Implant Therapy

Efficacy of Alloactivated Cells Prepared Using Third-Party Stimulators

Cell compositions were prepared, composed of either unstimulated allogeneic cells alone, allo-activated syngeneic cells, syn-activated allogeneic cells or alloactivated allogeneic cells (two separate allogeneic cells), or all-activated allogeneic cells (two separate allogeneic donors). Splenocytes form the mice were used to produce the alloactivated cells by culturing at a ratio of 10:1 responder:stimulator cells. Splenocyte combinations were cultured in RPMI plus 10% fetal calf serum (FCS) supplemented with penicillin-streptomycin at $3 \times 10^6$/mL at 37° C. for 3 days.

$1 \times 10^6$ live J588L lymphoma cells were admixed with $10 \times 10^6$ cultured mouse splenocytes, and then injected into the subcutaneous tissue over the right flank of Balb/c mice. Treated mice were watched for tumor growth for 3 weeks.

Mice without tumor were rechallenged 1 month later with $1 \times 10^6$ live lymphoma cells alone by left flank subcutaneous injections, and watched for tumor growth.

Figure 5:
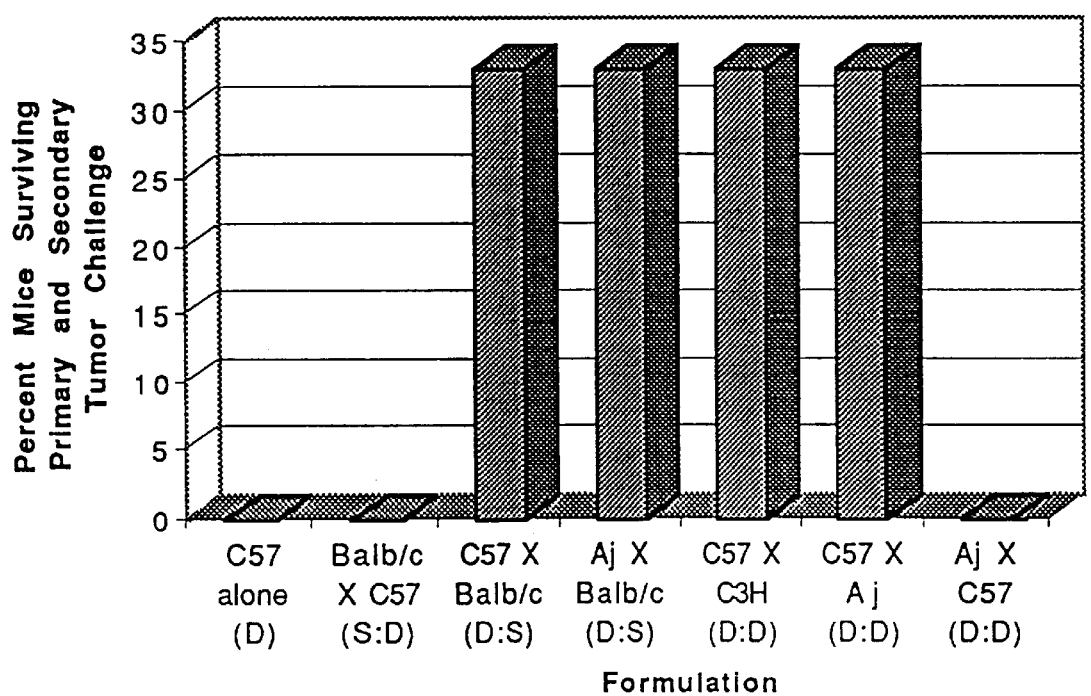
FIG. 5 is a bar graph showing the effect of different alloactivated lymphocyte preparations on providing resistance to a secondary challenge with J588L lymphoma cells in Balb/c mice. Allogeneic cells stimulated either with syngeneic splenocytes or certain third-party splenocytes are both effective.

FIG. 5 shows the results of these experiments. The presence of activated allogeneic cells correlates with a subsequent in vivo antitumor host response. Cell populations prepared using two donors allogeneic to the treated animal could be used in place of syngeneic or autologous cells in order to induce an antitumor response. However, not all combinations of activated allogeneic Donor:Donor cell populations were equally effective.

Correlation of Functional Markers with Antitumor Effect

To determine the correlation between in vitro functional assay results and potential therapeutic benefit, cultures showing various degrees of activation are tested in the mouse lymphoma treatment model. Mixed lymphocyte cultures are set up using splenocytes from a variety of inbred mouse strains at a 10:1 responder:stimulator cell ratio. Alternatively, cultures are set up using a particular responder: stimulator strain combination, but at different cell ratios. After three days of culture, the activity is measured in XTT Formazan assay and esterase assay.

Just before injection, the cultured cells are supplemented with additional splenocytes, as necessary, to normalize the cell ratio, and admixed with $1 \times 10^6$ live or irradiated J588L lymphoma cells. The preparation is the injected into Balb/c mice, and the effect on survival is monitored. The mice can be rechallenged with a subsequent dose of live lymphoma cells to test for a persisting immunological response. The survival data is then correlated with the functional activity measured during the culture period.

Antitumor Effect of Compositions Prepared using Cimetidine

As described elsewhere in this disclosure, histamine impairs alloactivation during the lymphocyte culture, as measured in the functional assays. Cimetidine, which is an H2 receptor antagonist, promotes alloactivation. In this study, alloactivation cultures are prepared in the presence or absence of 20 µg/mL histidine or cimetidine, tested in the XTT Formazan and esterase assays, and then injected into Balb/c mice with J588L lymphoma cells to correlate with efficacy.

Example 5: Clinical Trials

This example outlines the testing of implant compositions in conjunction with a peripherally administered cellular vaccine composition. The preparation and use of MLC tumor vaccines is described in more detail in International application WO 9618623, which is hereby incorporated herein by reference in its entirety.

All patients are enrolled with informed consent, and randomized into the various treatment groups. Tumor cells are obtained during surgical resection of the primary neoplasm, and cryopreserve at the time of surgery. The tumor cells are proliferated ex vivo if necessary to obtain sufficient cells for the anticipated course of therapy. Thawed or cultured tumor cells are subjected to 10,000 rads of gamma irradiation.

The mononuclear cells used to prepare each cellular vaccine are obtained from healthy, unrelated donors. Donors are prescreened to minimize risk for infectious diseases, and those that test positive are eliminated. By using genetically disparate donors, the likelihood of hyperacute rejection of the second administration is decreased. The mixed lymphocyte culture is conducted by mixing donor and inactivated patient peripheral blood mononuclear cells at a ratio of 10:1, and culturing at $3 \times 10^6$ cells/mL in AIMV supplemented with 2% fetal calf serum for 3 days at 37° C. The total number of mononuclear cells required for a single inoculum is no more than $1 \times 10^9$. The stimulated cells are collected and washed by centrifugation, then suspended in sterile, injectable saline. Quality control of the production of activated cells includes monitoring cell counts and viability, testing for mycoplasma and endotoxin, and monitoring for lymphocyte activation using early activation markers, as described in Example 1.

Before use in treatment, the alloactivated cell preparation is also evaluated according to functional release criteria. The Tetrazolium Reduction Assay (XTT) described in Example 1 is conducted on a cell sample. Flow Cytometry is conducted to measure cell surface expression of CD69 using fluorescent antibody; or increased intracellular esterase activity using fluorescein diacetate. Cultured cells are considered to be sufficiently activated if the level measured in either one (but preferably both) of these assays is $\geq 10\%$ above unstimulated donor control value on any day of the culture period (day 1, day 2, or day 3). Once the culture passes the criteria, testing on subsequent days is not needed. The cells are harvested on day 3, mixed with the requisite number of primary or cultured tumor cells, and prepared for human administration.

The study is conducted on patients with Stage IV (metastatic) colon cancer. Patents are enrolled in the study under terms of informed consent, and undergo a standard colectomy. About 1 week later (around the time they are discharged from the hospital), they begin a course of four vaccine injections.

The vaccine composition consists essentially of an alloactivated cell population mixed with tumor cells. Patients receive one of three different doses: $1 \times 10^8$ MLC cells; $3 \times 10^8$ MLC cells; or $1 \times 10^9$ MLC, mixed with up to $1 \times 10^7$ inactivated tumor cells, depending on availability. The same dose is given four times on a weekly schedule.

Initial studies are conducted primarily to determine the maximum tolerated dose (MTD). Undesirable clinical side effects at the injection site include an unacceptable level of induration, inflammation, or ulceration.

Once the MTD is determined, a comparison is made between the 4-week vaccination schedule alone, and a vaccination course initiated by direct implantation into a tumor mass. The implant group is treated two days to a week after colectomy, using ultrasound to guide an injection needle into a sizeable metastatic tumor mass in the liver. The metastatic site is injected with a preparation of $10 \times 10^9$ MLC alloactivated cells alone, suspended in a minimum volume of saline. Beginning one week later, the patients in this group also receive the 4-week course of the MLC-tumor cell vaccine.

Safety of the compositions is monitored by several criteria, including local induration, pruritus, or necrosis at the injection site; systemic effects such as fever, malaise, headache, and altered hematological or renal parameters.

The presence of a cellular immune response in the treated patient can be monitored by several criteria. Patient lymphocytes obtained before and after each inoculation are cultured with irradiated allogeneic cells of donor origin or from a third party (for antiallotype response), or irradiated patient tumor cells, or third-party tumor cells (for specific anti-tumor response). The response of patient lymphocytes in culture is determined by measuring proliferation using reduction of MTT or one of the other functional assays as a surrogate marker for cellular division. Expression of CD69 is determined by immunofluorocytometry using PE-labeled antibody.

Optionally, the responding T cells are costained for CD4, CD8, or CD31 to identify helper or suppressor subsets, or for CD45RF to distinguish $T_{H1}$ from $T_{H2}$ cells. Cytokines IL-2, IL-4, IFN-γ and TNF-α secreted into the culture media are quantified by ELISA. IL-2 and IFN-γ correlate with $T_{H1}$ activity, IL-4 correlates wit $T_{H2}$ activity, and TNF-α correlates with the activity of both. Patients' PBL are also optionally tested for their ability to respond to autologous tumor cells in culture. General T cell activation can be measured by the functional assays described in Example 1, [$^3$H] thymidine incorporation, or blastogenesis. Cytotoxic T cell activity can be measured as cytolysis of $^{51}$Cr labeled tumor cells. The effective delayed type hypersensitivity (DTH) anti-tumor response in the treated patient is measured by comparing the 48-hour response of the intradermal administration of 5×10$^5$ autologous tumor cells, mumps, tricophyton, or PPD antigens with that observed for the same series before treatment.

The patients are monitored for the extent of the clinical and immunological response for at least three months following therapy. Clinical criteria is monitored, in part, by tracking the volume of tumor metastasis present in the liver. A CT scan is performed at regular intervals, the volume of each metastatic site is calculated, and the volumes are compared with the measurements obtained before treatment. Progression of disease is indicated by an increase in volume of the metastasis, or an increase in the number of metastatic sites. A successful outcome is indicated by reversal of the disease, or slower progression in comparison with the typical outcome for patents with colon cancer of the same grade.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

What is claimed as the invention is:

1. A method of preparing a cultured cell population containing alloactivated human donor lymphocytes for administration to a human patient, comprising the steps of:
   a) coculturing human lymphocytes allogeneic to the human patient ex vivo with human leukocytes allogeneic to the lymphocytes so as to alloactivate the lymphocytes;
   b) harvesting the cocultured cells; and
   c) preparing the harvested cells for human administration;
   wherein the coculturing of step a) is conducted in a medium containing an H2 receptor antagonist.

2. The method of claim 1, wherein the human leukocytes allogeneic to the lymphocytes are obtained form the patient.

3. The method of claim 1, wherein the human leukocytes allogeneic to the lymphocytes are obtained from a donor other than the patient.

4. The method of claim 1, wherein the H2 receptor antagonist is cimetidine.

5. The method of claim 1, wherein the cimetidine is present in the culture medium at a concentration between about 5 μg/mL and about 100 μg/mL.

6. A cell population prepared according to the method of claim 1, which, upon implantation at or around the site of a solid tumor in a human patient with or without partial resection of the tumor, is effective in eliciting an immunological response to the solid tumor.

7. A cell population prepared according to the method of claim 1, which, upon implantation at or around the site of a solid tumor in a human patient with or without partial resection of the tumor, is effective in the treatment of the tumor.

8. The cell population of claim 7, wherein the tumor is selected from the group consisting of melanoma, pancreatic cancer, liver cancer, colon cancer, prostate cancer, and breast cancer.

* * * * *